United States Patent [19]

Ackermann et al.

[11] Patent Number: 4,587,255

[45] Date of Patent: May 6, 1986

[54] ISOMERS OF 3-(2,2-DICHLOROVINYL)-2,2-DIMETHYL-CYCLOPROPANECARBOXYLIC ACID-α-METHYL-(6-PHENOXY-2-PICOLYL)ESTER, PROCESSES FOR PRODUCING THEM, AND THEIR USE FOR CONTROLLING PESTS

[75] Inventors: Peter Ackermann, Pfeffingen; Laurenz Gsell, Basel; Boris Kohler, Binningen, all of Switzerland

[73] Assignee: Ciba-Geigy Corporation, Ardsley, N.Y.

[21] Appl. No.: 559,544

[22] Filed: Dec. 8, 1983

[30] Foreign Application Priority Data

Dec. 14, 1982 [CH] Switzerland .......................... 7271/82
Nov. 16, 1983 [CH] Switzerland .......................... 6157/83

[51] Int. Cl.[4] .................. A01N 43/40; C07D 213/64
[52] U.S. Cl. ..................................... 514/345; 546/302
[58] Field of Search ................. 546/302; 424/263; 514/345

[56] References Cited

U.S. PATENT DOCUMENTS 4,323,574  4/1982  Henrick .............................. 514/345

OTHER PUBLICATIONS

March, Advanced Organic Chemistry, Reactions, Mechanisms and Structure, Second Edition, pp. 108–113, McGraw-Hill Pub., 1977.

Primary Examiner—Alan L. Rotman
Attorney, Agent, or Firm—Edward McC. Roberts; Kevin T. Mansfield

[57] ABSTRACT

Novel isomers of the compound of the formula

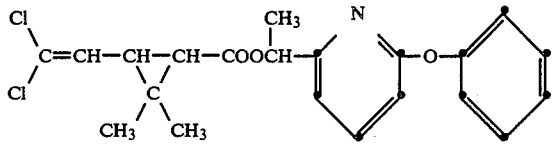

are described, and processes for producing these compounds and their use for controlling pests are given.

9 Claims, No Drawings

ISOMERS OF 3-(2,2-DICHLOROVINYL)-2,2-DIMETHYLCYCLOPROPANECARBOXYLIC ACID-α-METHYL-(6-PHENOXY-2-PICOLYL)ESTER, PROCESSES FOR PRODUCING THEM, AND THEIR USE FOR CONTROLLING PESTS

The present invention relates to novel isomers of 3-(2,2-dichlorovinyl)-2,2-dimethylcyclopropanecarboxylic acid-α-methyl-(6-phenoxy-2-picolyl)ester, to processes for producing them, and to their use for controlling pests.

These isomers, which have the formula

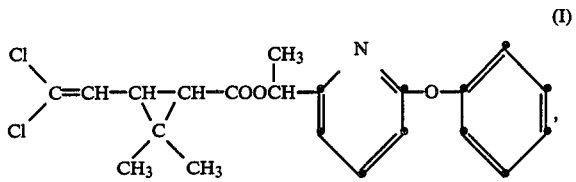

are:

(a) 1 R-cis-3-(2,2-dichlorovinyl)-2,2-dimethylcyclopropanecarboxylic acid-R,S-α-methyl-(6-phenoxy-2-picolyl)ester;

(b) 1 R-cis-3-(2,2-dichlorovinyl)-2,2-dimethylcylopropanecarboxylic acid-R-α-methyl-(6-phenoxy-2-picolyl)ester;

(c) 1 R-cis-3-(2,2-dichlorovinyl)-2,2-dimethylcyclopropanecarboxylic acid-S-α-methyl-(6-phenoxy-2-picolyl)ester;

(d) 1 R-trans-3-(2,2-dichlorovinyl)-2,2-dimethylcyclopropanecarboxylic acid-R,S-α-methyl-(6-phenoxy-2-picolyl)ester;

(e) 1 R-trans-3-(2,2-dichlorovinyl)-2,2-dimethylcyclopropanecarboxylic acid-R-α-methyl-(6-phenoxy-2-picolyl)ester; and (f) 1 R-trans-3-(2,2-dichlorovinyl)-2,2-dimethylcyclopropanecarboxylic acid-S-α-methyl-(6-phenoxy-2-picolyl)ester.

The compounds of the formula I are produced by methods known per se, for example as follows:

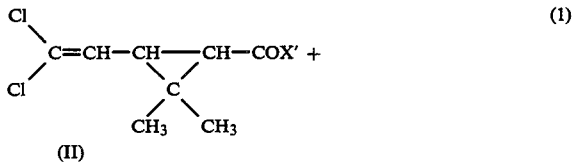

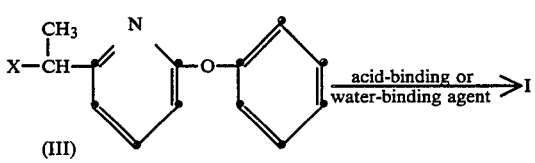

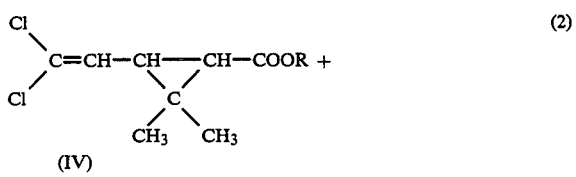

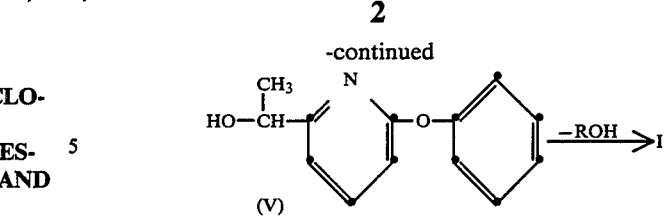

In the formulae II and III, the symbols X and X' are each a hydroxyl group, or one is a hydroxyl group and the other a halogen atom, particularly chlorine or bromine, In the formula IV, the symbol R is $C_1$–$C_4$-alkyl, especially methyl or ethyl.

Suitable acid-binding agents are in particular tertiary amines, such as trialkylamines and pyridine, also hydroxides, oxides, carbonates and bicarbonates of alkali metals and alkaline-earth metals, as well as alkali metal alcoholates, for example potassium tert-butylate and sodium methylate. The water-binding agent used can be for example bicyclohexylcarbodiimide. The processes 1 and 2 are performed at a reaction temperature of between −10° and 120° C., usually between 20° and 80° C., under normal or elevated pressure and preferably in an inert solvent or diluent. Suitable solvents or diluents are for example: ethers and ethereal compounds, such as diethyl ether, dipropyl ether, dioxane, dimethoxyethane and tetrahydrofuran; amides, such as N,N-dialkylated carboxylic acid amides; aliphatic, aromatic as well as halogenated hydrocarbons, especially benzene, toluene, xylenes, chloroform and chlorobenzene; nitriles, such as acetonitrile; dimethyl sulfoxide and ketones, such as acetone and methyl ethyl ketone.

The diastereoisomeric mixtures produced by the processes 1 and 2 can be separated by chromatography into the optically pure isomers.

The compounds II and IV are known as pure isomers and as isomeric mixtures, and the compounds of the formulae III and V only as isomeric mixtures, and can be produced by methods analogous to known methods.

The isomers of the formula I are suitable for controlling various pests on animals and plants. These compounds can be used for example to control insects, for example of the orders: Lepidoptera, Coleoptera, Homoptera, Heteroptera, Diptera, Thysanoptera, Orthoptera, Anoplura, Siphonaptera, Mallophaga, Thysanura, Isoptera, Psocoptera and Hymenoptera; and also mites and ticks of the order Acarina.

Compounds of the formula I are suitable in particular for controlling insects that damage plants, especially insects that damage plants by eating, in crops of ornamental plants and productive plants, particularly in cotton and rice crops (for example against *Spodoptera littoralis, Heliothis virescens, Chilo suppressalis* and Laodelphax), and also in vegetable crops (for example against *Leptinotarsa decemlineata*). The active substances of the formula I exhibit a very favourable action also against flies, such as *Musca domestica*, and againt mosquito larvae, and also against ectoparasitic mites and ticks, for example of the families: Ixodidae, Argasidae and Dermanyssidae. Furthermore, the compounds of the formula I are distinguished by a broad ovicidal and ovilarvicidal action.

The insecticidal spectrum of activity of the isomers of the formula I is achieved by application of the isomers in amounts that are surprisingly much smaller than those required to obtain the same effect using the isomeric mixtures of 3-(2,2-dichlorovinyl)-2,2-dimethylcyclopropanecarboxylic acid-α-methyl-(6-phenoxy-2-picolyl)ester known from the U.S. Pat. No. 4,323,574.

The acaricidal and insecticidal activity can be considerably broadened and adapted to suit given circumstances by the addition of further insecticides and/or acaricides. Suitable additives are for example: organic phosphorus compounds; nitrophenols and derivatives thereof; formamidines; ureas; other pyrethrin-like compounds, as well as carbamates and chlorinated hydrocarbons.

Compounds of the formula I are combined with particular advantage also with substances which have a synergistic or intensifying effect on pyrethroids. Examples of such compounds are, inter alia: piperonylbutoxide, propynyl ethers, propynyl oximes, propynyl carbamates and propynyl phosphonates, 2-(3,4-methylenedioxyphenoxy)-3,6,9-trioxaundecane (Sesamex or Sesoxane), S,S,S-tributylphosphorotrithioates and 1,2-methylenedioxy-4-(2-(octylsulfinyl)-propyl)benzene.

The compounds of the formula I are used either in an unmodified form or preferably together with auxiliaries customarily employed in formulation practice, and are thus processed in a known manner for example into the form of emulsion concentrates, directly sprayable or dilutable solutions, diluted emulsions, wettable powders, soluble powders, dusts or granulates, and also encapsulations in for example polymeric substances. The application processes, such as spraying, atomising, dusting, scattering or pouring, and likewise the type of composition, are selected to suit the objectives to be achieved and the given conditions.

The formulations, that is to say, the compositions or preparations containing the active ingredient of the formula I and optionally a solid or liquid additive, are produced in a known manner, for example by the intimate mixing and/or grinding of the active ingredients with extenders, such as with solvents, solid carriers and optionally surface-active compounds (tensides).

Suitable solvents are: aromatic hydrocarbons, preferably the fractions $C_8$ to $C_{12}$, such as xylene mixtures or substituted naphthalenes, phthalic esters, such as dibutyl- or dioctylphthalate, aliphatic hydrocarbons, such as cyclohexane or paraffins, alcohols and glycols, as well as ethers and esters thereof, such as ethanol, ethylene glycol, ethylene glycol monomethyl or -ethyl ethers, ketones such as cyclohexanone, strongly polar solvents, such as N-methyl-2-pyrrolidone, dimethyl sulfoxide or dimethylformamide, as well as optionally epoxidised vegetable oils, such as epoxidised coconut oil or soybean oil; or water.

The solid carriers used, for example for dusts and dispersible powders, are as a rule natural mineral fillers, such as calcite, talcum, kaolin, montmorillonite or attapulgite. In order to improve the physical properties, it is also possible to add highly dispersed silicic acid or highly dispersed absorbent polymers. Suitable granulated adsorptive carriers are porous types, for example pumice, ground brick, sepiolite or bentonite; and suitable nonsorbent carriers are materials such as calcite or sand. There can also be used a great number of pregranulated materials of inorganic or organic nature, such as in particular dolomite or ground plant residues.

Suitable surface-active compounds are, depending on the nature of the active ingredient of the formula I to be formulated, nonionic, cationic and/or anionic tensides having good emulsifying, dispersing and wetting properties. By 'tensides' are also meant mixtures of tensides.

Suitable anionic tensides are both so-called water-soluble soaps as well as water-soluble, synthetic, surface-active compounds.

Soaps which are applicable are the alkali metal, alkaline-earth metal or optionally substituted ammonium salts of higher fatty acids ($C_{10}$–$C_{22}$), for example the Na or K salts of oleic or stearic acid, or of natural fatty acid mixtures, which can be obtained for example from coconut oil or tallow oil. Also to be mentioned are the fatty acid-methyl-taurine salts.

So-called synthetic tensides are however more frequently used, particularly fatty sulfonates, fatty sulfates, sulfonated benzimidazole derivatives or alkylarylsulfonates. The fatty sulfonates or sulfates are as a rule in the form of alkali metal, alkaline-earth metal or optionally substituted ammonium salts, and contain an alkyl group having 8 to 22C atoms, 'alkyl' including also the alkyl moiety of acyl groups, for example the Na or Ca salt of ligninsulfonic acid, of dodecylsulfuric acid ester or of a fatty alcohol sulfate mixture produced from natural fatty acids. Included among these are also the salts of sulfuric acid esters and sulfonic acids of fatty alcohol ethylene oxide adducts. The sulfonated benzimidazole derivatives preferably contain 2 sulfonic acid groups and a fatty acid group having 8–22C atoms. Alkylarylsulfonates are for example the Na, Ca or triethanolamine salts of dodecylbenzenesulfonic acid, of dibutylnaphthalenesulfonic acid, or of a naphthalenesulfonic acid-formaldehyde condensation product. Also suitable are corresponding phosphates, for example salts of the phosphoric ester of a p-nonylphenol-(4–14)-ethylene oxide adduct, and phospholipids.

Suitable nonionic tensides are in particular polyglycol ether derivatives of aliphatic or cycloaliphatic alcohols, saturated or unsaturated fatty acids and alkylphenols, which can contain 3 to 30 glycol ether groups and 8 to 20 carbon atoms in the (aliphatic) hydrocarbon radical and 6 to 18 carbon atoms in the alkyl moiety of the alkylphenols.

Further suitable nonionic tensides are the water-soluble polyethylene oxide adducts, which contain 20 to 250 ethylene glycol ether groups and 10 to 100 propylene glycol ether groups, with polypropylene glycol, ethylenediaminopolypropylene glycol and alkylpolypropylene glycol having 1 to 10 carbon atoms in the alkyl chain. The compounds mentioned usually contain 1 to 5 ethylene glycol units per propylene glycol unit. Examples of nonionic tensides which may be mentioned are: nonylphenol-polyethoxyethanols, castor oil polyglycol ethers, polypropylene/polyethyleneoxy adducts, tributylphenoxy-polyethoxyethanol, polyethylene glycol and octylphenoxy-polyethoxyethanol. Suitable also are fatty acid esters of polyoxyethylenesorbitan, such as polyoxyethylenesorbitan-trioleate.

In the case of the cationic tensides, they are in particular quaternary ammonium salts which contain as N-substituents at least one alkyl group having 8 to 22C atoms and, as further substituents, lower, optionally halogenated alkyl, benzyl or lower hydroxyalkyl groups. The salts are preferably in the form of halides, methyl sulfates or ethyl sulfates, for example stearyltrimethylammonium chloride or benzyldi(2-chloroethyl)ethylammonium bromide.

The tensides customarily used in formulation practice are described, inter alia, in the following publications: "Mc Cutcheon's Detergents and Emulsifiers Annual", MC Publishing Corp., Ringwood, N.J., 1979; and Dr.

Helmut Stache "Tensid Taschenbuch", Carl Hauser Verlag, Munich/Vienna, 1981.

The pesticidal preparations contain as a rule 0.1 to 99%, particularly 0.1 to 95%, of active ingredient of the formula I, 1 to 99.9% of a solid or liquid additive, and 0 to 25%, especially 0.1 to 25% of a tenside.

Whereas commercial products are preferably in the form of concentrated compositions, the compositions employed by the end-user are as a rule diluted.

The compositions can also contain further additives such as stabilisers, antifoam agents, viscosity regulators, binders and adhesives, as well as fertilisers or other active ingredients for obtaining special effects.

Formulation examples for liquid active ingredients of the formula I (%=percent by weight)

| 1. Emulsion concentrates | (a) | (b) | (c) |
|---|---|---|---|
| active ingredient | 25% | 40% | 50% |
| calcium dodecylbenzenesulfonate | 5% | 8% | 6% |
| castor oil-polyethylene glycol ether (36 mols of ethylene oxide) | 5% | — | — |
| tributylphenol-polyethylene glycol ether (30 mols of ethylene oxide) | — | 12% | 4% |
| cyclohexanone | — | 15% | 20% |
| xylene mixture | 65% | 25% | 20% |

Emulsions of any required concentration can be produced from concentrates of this type by dilution with water.

| 2. Solutions | (a) | (b) | (c) | (d) |
|---|---|---|---|---|
| active ingredient | 80% | 10% | 5% | 95% |
| ethylene glycol-monomethyl ether | 20% | — | — | — |
| polyethylene glycol M.W. 400 | — | 70% | — | — |
| N—methyl-2-pyrrolidone | — | 20% | — | — |
| epoxidised coconut oil | — | — | 1% | 5% |
| ligroin (boiling limits 160–190° C.) | — | — | 94% | — |

These solutions are suitable for application in the form of very small drops.

| 3. Granulates | (a) | (b) |
|---|---|---|
| active ingredient | 5% | 10% |
| kaolin | 94% | — |
| highly dispersed silicic acid | 1% | — |
| attapulgite | — | 90% |

The active ingredient is dissolved in methylene chloride, the solution is sprayed onto the carrier, and the solvent is subsequently evaporated off in vacuo.

| 4. Dusts | (a) | (b) |
|---|---|---|
| active ingredient | 2% | 5% |
| highly dispersed silicic acid | 1% | 5% |
| talcum | 97% | — |
| kaolin | — | 90% |

Ready-for-use dusts are obtained by the intimate mixing together of the carriers with the active ingredient.

Formulation examples for solid active ingredients of the formula I (%=percent by weight)

| 5. Wettable powders | (a) | (b) | (c) |
|---|---|---|---|
| active ingredient | 25% | 50% | 75% |
| sodium lignin sulfonate | 5% | 5% | — |
| sodium lauryl sulfate | 3% | — | 5% |
| sodium diisobutylnaphthalene sulfonate | — | 6% | 10% |
| octylphenolpolyethylene glycol ether (7-8 mols of ethylene oxide) | — | 2% | — |
| highly dispersed silicic acid | 5% | 10% | 10% |
| kaolin | 62% | 27% | — |

The active ingredient is well mixed with the additives and the mixture is thoroughly ground in a suitable mill. Wettable powders which can be diluted with water to give suspensions of the required concentration are obtained.

| 6. Emulsion concentrate | |
|---|---|
| active ingredient | 10% |
| octylphenol polyethylene glycol ether (4-5 mols of ethylene oxide) | 3% |
| calcium dodecylbenzene sulfonate | 3% |
| castor oil polyglycol ether (36 mols of ethylene oxide) | 4% |
| cyclohexanone | 30% |
| xylene mixture | 50% |

Emulsions of the concentration required can be obtained from this concentrate by dilution with water.

| 7. Dusts | (a) | (b) |
|---|---|---|
| active ingredient | 5% | 8% |
| talcum | 95% | — |
| kaolin | — | 92% |

Dusts ready for use are obtained by mixing the active ingredient with the carrier, and grinding the mixture in a suitable mill.

| 8. Extruder granulate | |
|---|---|
| active ingredient | 10% |
| sodium lignin sulfonate | 2% |
| carboxymethyl cellulose | 1% |
| kaolin | 87% |

The active ingredient is mixed and ground with the additives, and the mixture is moistened with water. This mixture is extruded and then dried in a stream of air.

| 9. Coated granulate | |
|---|---|
| active ingredient | 3% |
| polyethylene glycol (M.W. 200) | 3% |
| kaolin | 94% |

The finely ground active ingredient is evenly applied, in a mixer, to the kaolin moistened with polyethylene glycol. Dustfree coated granulates are obtained in this manner.

| 10. Suspension concentrate | |
|---|---|
| active ingredient | 40% |
| ethylene glycol | 10% |
| nonylphenolpolyethylene glycol ether (15 mols of ethylene oxide) | 6% |
| sodium lignin sulfonate | 10% |
| carboxymethyl cellulose | 1% |
| 37% aqueous formaldehyde solution | 0.2% |

-continued

| 10. Suspension concentrate | |
|---|---|
| silicone oil in the form of a 75% aqueous emulsion | 0.8% |
| water | 32% |

The finely ground active ingredient is intimately mixed with the additives. There is obtained a suspension concentrate from which can be produced, by dilution with water, suspensions of the concentration required.

EXAMPLE 1

1

R-cis-3-(2,2-Dichlorovinyl)-2,2-dimethylcyclopropanecarboxylic acid-R,S-α-methyl-(6-phenoxy-2-picolyl)methyl ester To an ice-cooled solution of 3.2 g of 1 R-cis-3-(2,2-dichlorovinyl)-2,2-dimethylcyclopropanecarboxylic acid chloride in 20 ml of toluene there are added successively 1.4 g of pyridine, dissolved in 5 ml of toluene, and then 3 g of 1-(6-phenoxy-2-pyridyl)-ethanol in 10 ml of toluene. An addition of 200 mg of 4-dimethylaminopyridine is made to the slightly yellowish suspension, and the reaction mixture is stirred for 16 hours at room temperature. After the addition of 100 ml of toluene, the organic phase is washed with ice-cooled 1N HCl solution, 10% K$_2$CO$_3$ solution, saturated NaHCO$_3$ solution and saturated sodium chloride solution, and dried over MgSO$_4$. The solvent is then removed under reduced pressure and the crude product is purified on silica gel with toluene as the eluant. There is thus obtained a diastereoisomeric (1:1) mixture (a) of the following structure:

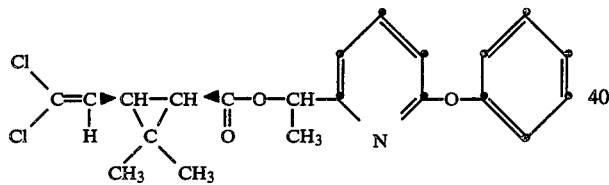

having a refractive index of
$n_D^{20°} = 1.5447$,
and an optical rotation of
$[\alpha]_D = +23° \pm 1°$ [c=1.06 in benzene].

The diastereoisomeric mixture is chromatographically separated into the optically pure isomers (b) and (c) (silica gel, with toluene/hexane=95:5 as eluant).

The isomer (b) is first eluted and has the following physical data:
$n_D^{20°} = 1.5605$,
$[\alpha]_D = +116° \pm 1°$ [c=1.07 in benzene].
The isomer (c) is characterised by
$n_D^{20°} = 1.5591$,
$[\alpha]_D = -69° \pm 1°$ [c=0.937 in benzene].

In an analogous manner is produced also the 1 R-trans-3-(2,2-dichlorovinyl)-2,2-dimethylcyclopropanecarboxylic acid-R,S-α-methyl-(6-phenoxy-2-picolyl)ester (d) having a refractive index of
$n_D^{20°} = 1.5591$,
and an optical rotation of
$[\alpha]_D = +1°$ [c=0, in chloroform].

The diastereoisomeric mixture is separated by chromatography into the optically pure isomers (e) and (f).
The isomer (e) has the following physical data:

$n_D^{20°} = 1.5581$,
$[\alpha] = +77°$ [c=0.74 in benzene];
and the isomer (f)
$n_D^{21°} = 1.5581$,
$[\alpha] = -56°$ [c=0.83 in benzene].

EXAMPLE 2

Insecticidal stomach-poison action

Cotton plants are sprayed with a test solutions containing 1.25, 0.6 and 0.3 g, respectively, of the compound to be tested per 100 liters of H$_2$O. After the drying of the coating, larvae of the species Heliothis virescens (L$_1$ stage) are settled onto the plants. Two plants are used per test compound, and an evaluation of the mortality rate achieved is made after 24 and 48 hours. The test is carried out at 24° C. with 60° relative humidity.

Compounds according to the Production Example 1 exhibit against larvae of the species Heliothis virescens the action shown in the following Table.

| Mortality rate in % of Heliothis virescens L$_1$ larvae | | | | | | |
|---|---|---|---|---|---|---|
| Concentration | 1.25 g | | 0.6 g | | 0.3 g | |
| Compounds | 24 | 48 | 24 | 48 | 24 | 48 hours |
| (a) | 50 | 83 | 38 | 60 | 20 | 33 |
| (b) | 43 | 90 | 43 | 77 | 28 | 55 |
| isomeric mixture of formula (g)* known from U.S. Pat. No. 4,323,574 | 15 | 20 | 0 | 0 | 0 | 0 |

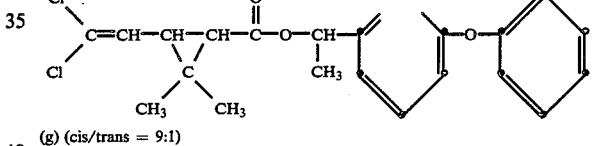

(g) (cis/trans = 9:1)

EXAMPLE 3

Action against ticks (A) Amblyomma hebraeum

For each concentration, 5 nymphs are counted into a small glass test tube, and in each case immersed for 1 to 2 minutes in 2 ml of an aqueous emulsion from a dilution series of 10, 1 and 0.1 ppm of test substance. Each test tube is then sealed with a standardised cotton plug, and inverted so that the active-substance emulsion can be absorbed by the cotton wool. An evaluation is made after 1 week, and for each test there are two repeats carried out.

(B) Boophilus microplus (larvae)

With a dilution series analogous to that for Test (A), tests are carried out on 20 sensitive larvae and OP-resistant larvae, respectively (resistance is with respect to diazinon compatibility).

The compounds according to Production Example 1 exhibit the degree of activity shown in the following Table against nymphs and larvae of the ticks: Amblyomma hebraeum and Boophilus microplus, respectively.

Biological test results

The Table which follows summarises the test results on the basis of Example 3, the evaluation index with regard to the percentage mortality (killing) rate being as follows:

A: 70–100% mortality with 0.1 ppm of active ingredient
B: 70–100% mortality with 1 ppm of active ingredient
C: 70–100% mortality with 10 ppm of active ingredient

| Compounds | Mortality rate of | | |
|---|---|---|---|
| | *A. hebraeum* nymphs | Boophilus sens. larvae | OP-resistant larvae |
| (a) | A | A | A |
| (b) | A | A | A |
| (c) | B | B | B |
| (d) | B | B | B |
| (e) | B | B | C |
| (f) | B | B | C |

What is claimed is:

1. A R-cis or R-trans isomer of the formula

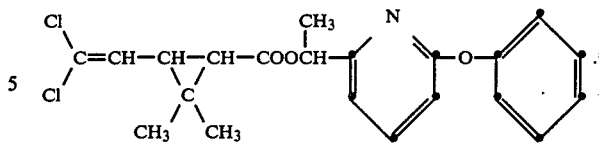

2. 1 R-cis-3-(2,2-Dichlorovinyl)-2,2-dimethylcyclopropanecarboxylic acid-R,S-α-methyl-(6-phenoxy-2-picolyl)ester according to claim 1.

3. 1 R-cis-3-(2,2-Dichlorovinyl)-2,2-dimethylcyclopropanecarboxylic acid-R-α-methyl-(6-phenoxy-2-picolyl)ester according to claim 1.

4. 1 R-cis-3-(2,2-Dichlorovinyl)-2,2-dimethylcyclopropanecarboxylic acid-S-α-methyl-(6-phenoxy-2-picolyl)ester according to claim 1.

5. 1 R-trans-3-(2,2-Dichlorovinyl)-2,2-dimethylcyclopropanecarboxylic acid-R,S-α-methyl-(6-phenoxy-2-picolyl)ester according to claim 1.

6. 1 R-trans-3-(2,2-Dichlorovinyl)-2,2-dimethylcyclopropanecarboxylic acid-R-α-methyl-(6-phenoxy-2-picolyl)ester according to claim 1.

7. 1 R-trans-3-(2,2-Dichlorovinyl)-2,2-dimethylcyclopropanecarboxylic acid-S-α-methyl-(6-phenoxy-2-picolyl)ester according to claim 1.

8. A pesticidal composition which contains an effective amount of a compound of claim 1 and an inert, pesticidally acceptable carrier.

9. A method of combating insects and acarids, which method comprises the step of applying thereto or to the locus thereof an effective amount of a compound of claim 1.

* * * * *